United States Patent [19]

Orr et al.

[11] Patent Number: 5,263,938

[45] Date of Patent: Nov. 23, 1993

[54] GUIDEWIRE INTRODUCER ASSEMBLY

[75] Inventors: Douglas P. Orr; Mark A. Crawford, both of Sandy, Utah

[73] Assignee: Becton, Dickinson and Company, Franklin Lakes, N.J.

[21] Appl. No.: 826,735

[22] Filed: Jan. 28, 1992

[51] Int. Cl.$^5$ .............................................. A61M 5/00
[52] U.S. Cl. ..................................................... 604/171
[58] Field of Search ................................. 604/51-53, 604/158, 159, 162, 163, 164, 170, 171, 177, 178, 280, 282; 128/657, 772

[56] References Cited

U.S. PATENT DOCUMENTS

| | | |
|---|---|---|
| 3,561,445 | 2/1971 | Katerndahl et al. . |
| 3,995,628 | 12/1976 | Gula et al. . |
| 4,160,451 | 7/1979 | Chittenden . |
| 4,405,314 | 9/1983 | Cope ............................... 604/51 |
| 4,425,908 | 1/1984 | Simon . |
| 4,515,592 | 5/1985 | Frankhouser ................... 604/171 X |
| 4,552,554 | 11/1985 | Gould et al. ...................... 604/51 |
| 4,650,472 | 3/1987 | Bates ............................... 604/170 X |
| 4,713,057 | 12/1987 | Hattner et al. .................. 604/164 |
| 4,799,496 | 1/1989 | Hargreaves et al. . |
| 4,860,757 | 8/1989 | Lynch et al. . |
| 4,917,094 | 4/1990 | Lynch et al. . |
| 4,969,875 | 11/1990 | Ichikawa ....................... 604/170 X |
| 4,976,697 | 12/1990 | Walder et al. .................. 604/164 |
| 4,995,872 | 2/1991 | Ferrara ........................... 604/280 |
| 5,073,164 | 12/1991 | Hollister et al. ............... 604/280 X |
| 5,125,905 | 6/1992 | Wright et al. .................. 604/171 |
| 5,125,906 | 6/1992 | Fleck ............................... 604/171 |

FOREIGN PATENT DOCUMENTS

| | | | |
|---|---|---|---|
| 2476476 | 8/1981 | France | 604/280 |
| 90/04994 | 5/1990 | PCT Int'l Appl. . | |
| 207358 | 12/1967 | U.S.S.R. . | |

OTHER PUBLICATIONS

Advertisement from the Journal of the American Society of Anesthesiologists, Inc., vol. 75, No. 1 (Jul. 1991).
Blitt, Wright, Petty and Webster, *Central Venous Catheterization via the External Jugular Vein*, JAMA vol. 229 No. 7 (Aug. 12, 1974).

Primary Examiner—Randall L. Green
Assistant Examiner—Mary Beth O. Jones
Attorney, Agent, or Firm—Michael G. Schwarz

[57] ABSTRACT

A guidewire introducer assembly is disclosed, together with a method of introducing a guidewire into a blood vessel. The introducer assembly allows a guidewire to be grasped between the digits of a user, thereby facilitating advancement or retraction of the guidewire. It includes an elongated dispenser tube, a guidewire slidably positioned within the dispenser tube and a guidewire introducer. The guidewire introducer includes or defines an opening through which the guidewire may be grasped. As the guidewire passes through the opening, it can be grasped by a user and advanced or retracted through the guidewire introducer. The guidewire introducer also allows the user to straighten the end portion of the guidewire. This allows the easy insertion of a guidewire having a J-tipped end portion within an introducer needle or catheter.

14 Claims, 7 Drawing Sheets

GUIDEWIRE INTRODUCER ASSEMBLY

BACKGROUND OF THE INVENTION

1. Field of the Invention

The present invention relates to guidewire introducers and, more particularly, to a quidewire introducer assembly for straightening the J tip of a guidewire.

2. Description of the Prior Art

Guidewires are well known in the prior art. Although employed in a number of contexts, typically they are used to introduce a catheter into a blood vessel. One known procedure generally includes the following steps: 1) inserting a cannula into a blood vessel; 2) feeding a guidewire through the cannula; 3) advancing the guidewire into the blood vessel until the tip of the guidewire is at the desired location; 4) removing the cannula; 5) sliding a catheter over the guidewire and inserting the catheter into the vessel; and 6) withdrawing the guidewire.

Several variations, well known in the art, exist on the above-described procedure. For example, sometimes it is necessary to first insert a guidewire of a particularly small diameter, over which a catheter can be inserted. The first guidewire is then withdrawn and a second guidewire of a larger diameter is inserted into the catheter. The first catheter is withdrawn and a second, larger catheter is inserted over the second, larger guidewire.

Guidewires are typically made from a tightly-wound steel wire of small diameter. Such a construction renders the guidewire sufficiently flexible for its intended use. Further, the guidewires may be of a straight design or may include a J-tip end portion. Guidewires having a straight design generally include a rounded tip portion to prevent the possibility of damaging the blood vessel during the insertion procedure. The coiled construction of such guidewire makes the guidewire susceptible to contamination if it is not handled correctly during an insertion procedure.

In contrast, the distal tip of a J-tip guidewire should not impact the wall of a blood vessel since the advancing portion is in the shape of a "J". Instead, only the gently curved section of the J-tip will contact the walls, thereby facilitating guidewire introduction and reducing the possibility of damaging the blood vessel during insertion thereof.

Since the introduction of J-tip guidewire, several patents have issued disclosing various methods for introducing and placing these guidewire at desired locations within a blood vessel. For example, U.S. Pat. No. 4,405,314 to Cope discloses an apparatus and method for catherization permitting use of a smaller gauge needle. The patent discloses an introducing catheter having a tapered tip which includes a side port such that when a J-tip guidewire is advanced within the catheter, the guidewire will automatically emerge from the side port. The guidewire can then be advanced to the desired location, at which point the introducing catheter is removed and a final catheter is slidably inserted over the J-tip guidewire. U.S Pat. No. 4,552,554 to Gould et al. improves on this apparatus and method for introducing J-tip guidewires. In particular, Gould et al. discloses an introducing catheter that is straight in design, yet still allows a J-tip guidewire to exit from a side port therein. Both of the above mentioned patents require the use of a specially manufactured introducing catheter.

SUMMARY OF THE INVENTION

The invention comprises a dispenser tube, a guidewire and a guidewire introducer. The guidewire is initially retained in the dispenser tube. As the guidewire exits the dispenser tube, it is received by the guidewire introducer, which attaches to, and preferably fits over, one end of the dispenser tube. The guidewire introducer includes an introducer which in turn includes an open portion, which is located between a front end portion and a rear end portion thereof. In the preferred embodiment the open portion is defined by a pair of curved or bowed members lying between the front and rear portions, although the open portion may be defined in a variety of ways including an opening in the upper or lower parts of the introducer.

The front end portion is designed to be removably attached and secured to a luer adapter typically found on introducer catheters. The rear end portion is attached to the dispenser tube. The guidewire extends through the open portion of the guidewire introducer and is in an easily accessible position to be manually advanced or retracted. It can also be twisted about its axis to reposition the tip if necessary. The open portion may be covered by a protective film or may accommodate a slidable sheath member covering part of the guidewire. The sheath or protective film provides a gripping surface, and insulates the guidewire from contact with the digits of a user thus reducing the risk of contamination.

A preferred method for introducing a guidewire into a vessel comprises the following steps: (1) inserting an introducer catheter into the vessel; (2) providing a guidewire introducer assembly; (3) inserting an end portion of the guidewire introducer assembly into an adapter of the introducer catheter; (4) grasping the guidewire extending through the guidewire introducer with a thumb and finger; and (5) advancing the guidewire through the catheter introducer and into the blood vessel.

For a better understanding of the present invention, together with other and further objects, reference is made to the following description, taken together with the accompanying drawings and description. It is to be understood that the drawings and description are designed for the purpose of illustration only and are not intended as a definition of the limits of the invention.

DETAILED DESCRIPTION

Figure 1:
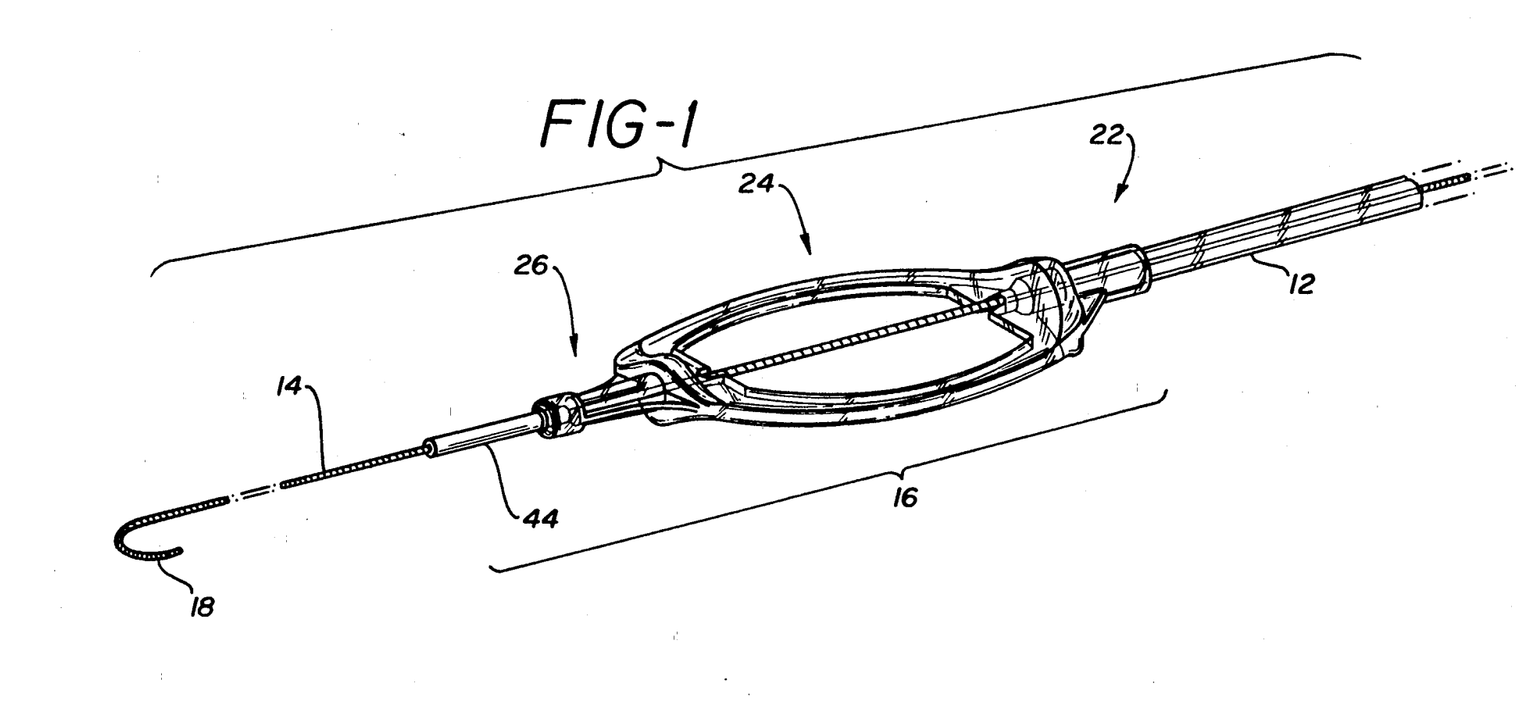
FIG. 1 is a perspective view of the preferred embodiment of the present invention.
Figure 2:
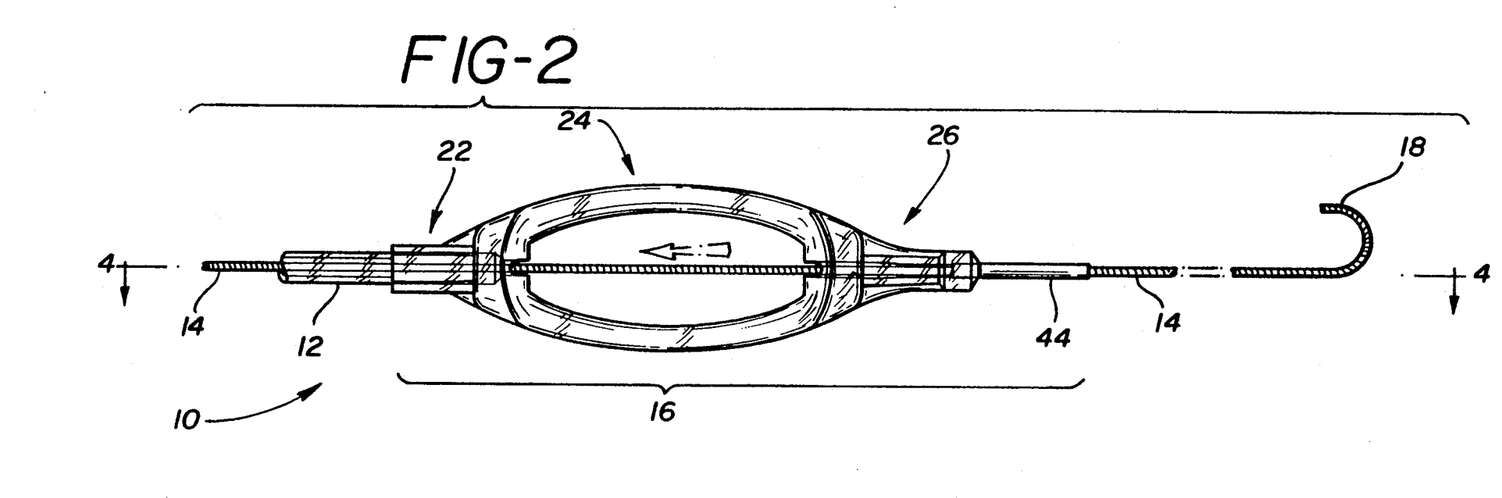
FIG. 2 is a top plan view thereof showing a J-tip guidewire being retracted therein.
Figure 3:
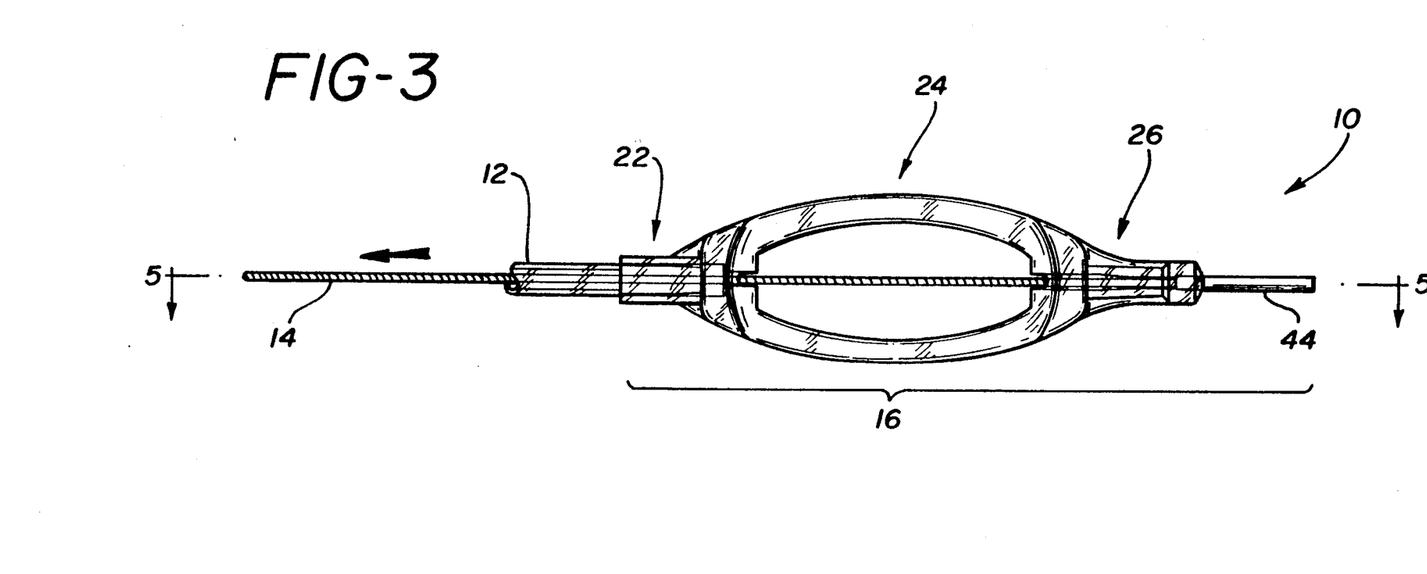
FIG. 3 is a top plan view thereof showing a J-tip guidewire retracted therein.

Turning now to the drawings, a guidewire introduce assembly 10 is shown in FIG. 1. Guidewire introducer assembly 10 comprises an elongated dispenser tube 12, a guidewire 14 and a guidewire introducer 16. The guidewire 14 preferably includes a J-tip end portion 18. The opposite end (not shown) of the guidewire 14 is preferably straight. As shown in FIGS. 1 and 2, the end portion 18 remains curved while in an extended position. When the guidewire 14 is retracted into the guidewire introducer 16, as shown in FIG. 3, the end portion 18 is straightened.

Figure 5:
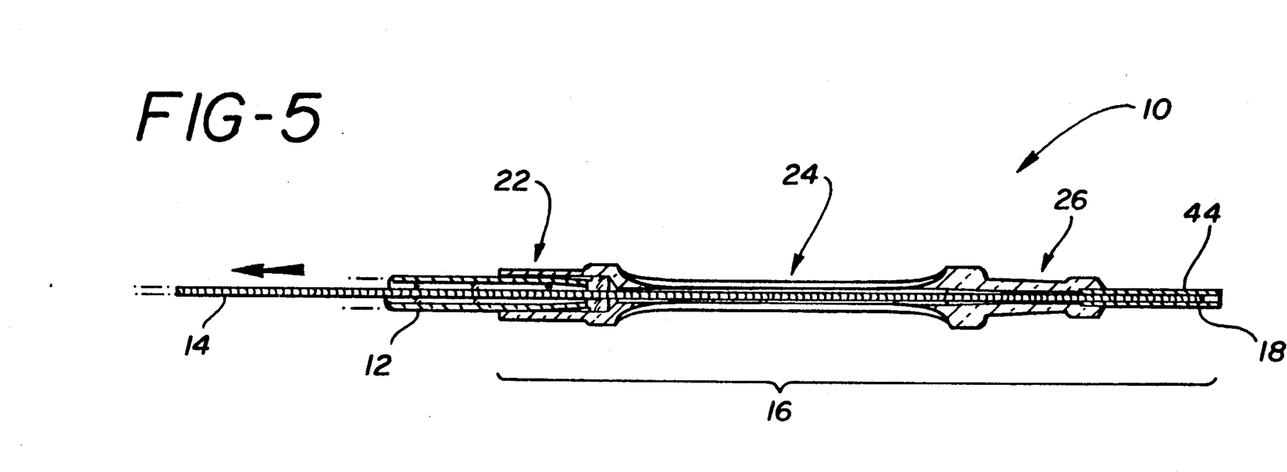
FIG. 5 is a cross-section thereof taken through line 5—5 of FIG. 3.
Figure 8:
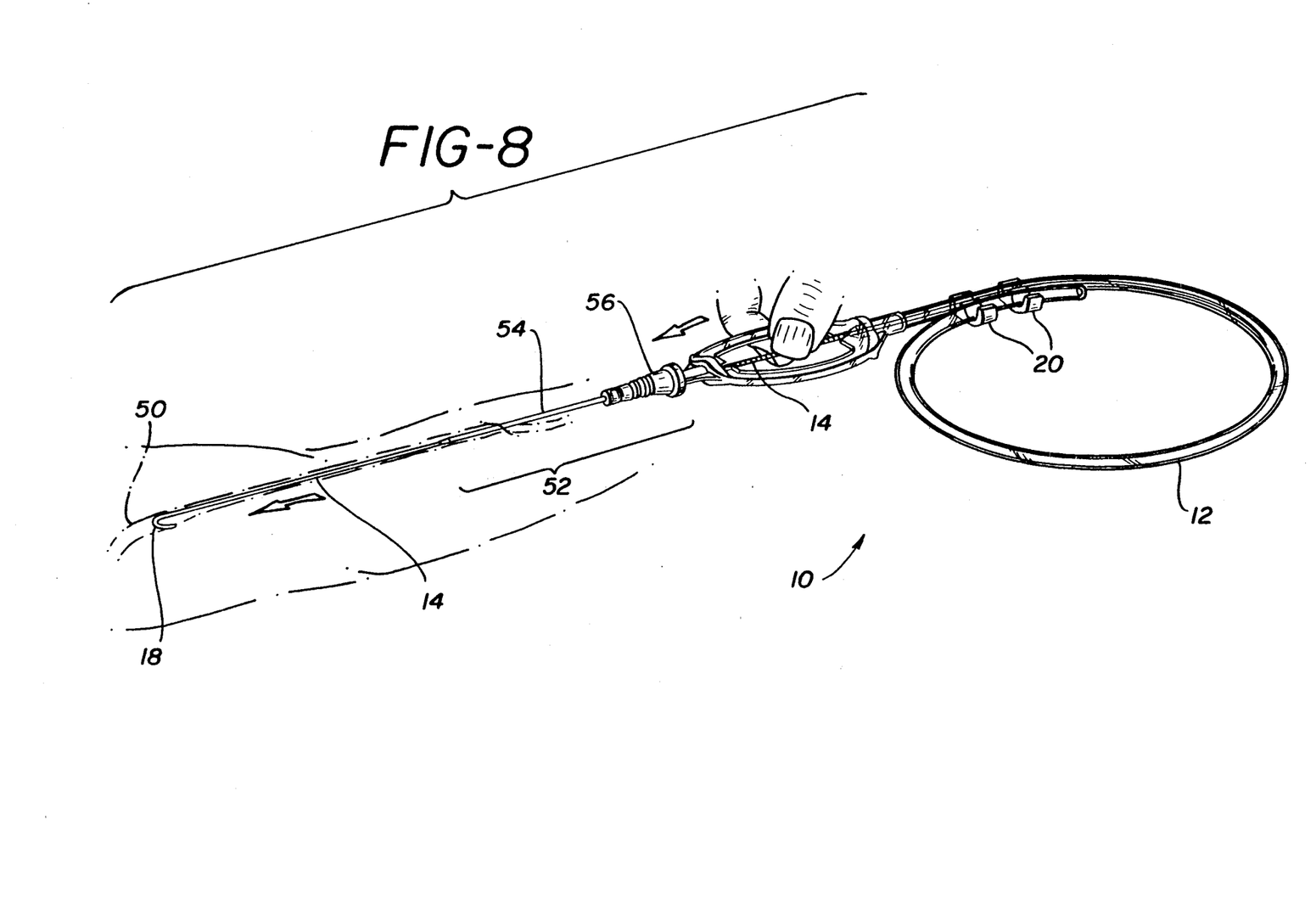
FIG. 8 is a top perspective view showing the introduction of a J-tip guidewire into a blood vessel.

Dispenser tube 12 comprises a length of flexible plastic tubing. The length of the dispenser tube 12 is such that when the end portion 18 of the guidewire 14 is withdrawn into the guidewire introducer 16, as shown in FIG. 5, the opposite end portion thereof remains within dispenser tube 12. The dispenser tube 12 has an internal diameter sufficiently larger than the external diameter of the guidewire 14 such that the guidewire slides easily therein. The dispenser tube 12 is maintained in a generally circular configuration by means of retaining clips 20, as shown in FIG. 8.

Figure 6:
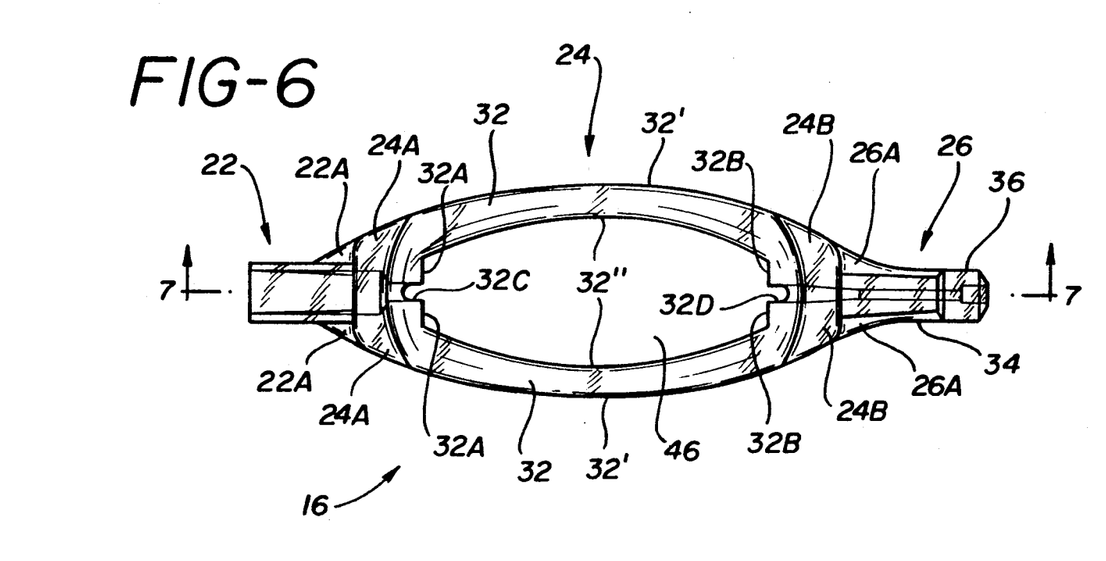
FIG. 6 is an enlarqed top plan view of the guidewire introducer of the preferred embodiment of the present invention.
Figure 7:
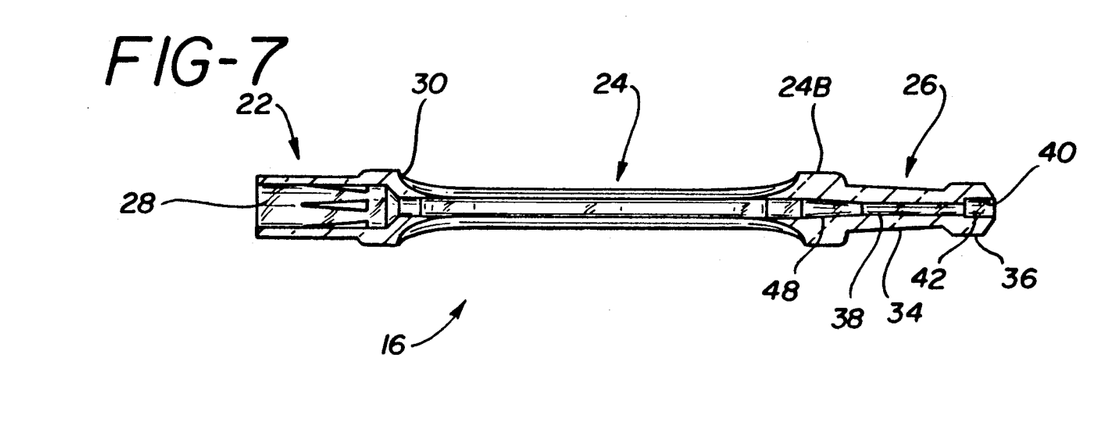
FIG. 7 is a cross section thereof taken through line 7—7 of FIG. 6.

The guidewire introducer 16, as best shown in FIGS. 6-7, is an integrally molded plastic unit having a first, rear end portion 22, an intermediate portion 24 and a second, tapered front end portion 26. It is preferably made from a semi-rigid, transparent material such as polycarbonate, but may also be made of butadiene styrene polymer or acrylic. While not preferred, the introducer could be incorporated as an integral portion of the dispenser tube 12. The rear end portion 22 includes a passage 28. The passage 28 has an inner diameter substantially the same as the outside diameter of dispenser tube 12. One end of the dispenser tube 12 may thus be inserted within passage 28 and maintained in position through a friction fit. The friction fit allows the guidewire introducer 16 to be rotated with respect to the dispenser tube 12. The dispenser tube 12 is inserted into passage 28 until it abuts a bevelled portion 30 at the end of the passage 28. The bevelled portion 30 is formed in base portion, 24A of the intermediate portion 24. Webbings 22A and 26A respectively connect the rear portion 22 and front portion 26 of the guidewire introducer with the intermediate portion 24 thereof, thereby forming a smooth, generally elliptical configuration as shown in FIG. 6.

In the preferred embodiment intermediate portion 24 comprises a pair of opposing bowed members 32 which define an opening 46 in introducer 16. The opening 46 may be defined by any space in introducer 16 which permits access to guidewire 14 so that it may be grasped and manipulated by the digits of the user. The bowed members 32 connect the rear portion 22 of the guidewire introducer 16 to the front portion 26 thereof. Each bowed member 32 is generally wedge shaped in cross section such that the outer edges 32' thereof are thicker than the inner edges 32". The top and bottom (outside) surfaces of the bowed members are substantially flat. A pair of webs, 32A and 32B, extend between the ends of the bowed members, at base portions 24A and 24B respectively as shown in FIG. 6. Each web 32A, 32B respectively includes a slot 32C, 32D extending therethrough and coaxial with the lonqitudinal axis of the passage 28 through the rear portion 22.

Figure 4:
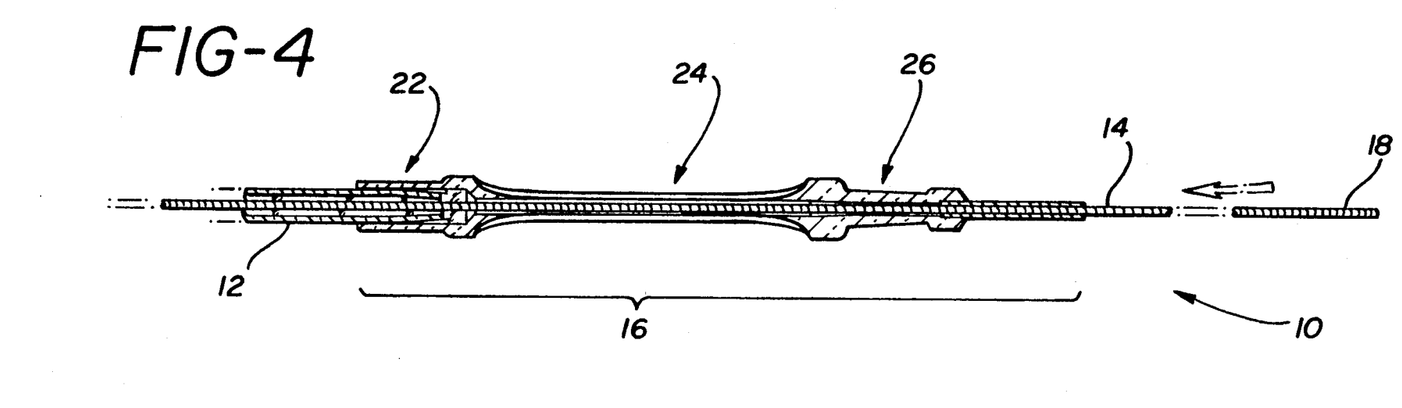
FIG. 4 is a cross-section thereof taken through line 4—4 of FIG. 2.

The front portion 26 of the guidewire introducer 16 includes an elongated, tubular body 34 which extends from the front base portion 24B of the intermediate portion 24 and includes an enlarged end portion 36. The end portion 36 is preferably dimensioned to be connected to a female luer connector. It could also be dimensioned for connection to a male luer fitting or other similar fitting. As used herein, the term "luer connector" contemplates well known "luer-lok" connectors for interconnecting devices such as catheters, hypodermic needles or the like to syringes or the like, and their equivalents. The outside diameter of the tubular body 34 decreases from the front base portion 24B towards the enlarged end portion 36. A passage 38 extends through the tubular body 34 and communicates with the slot 32D at one end and an enlarged passage 40 within the enlarged end portion 36. The passage 38 is substantially coaxial with the passage 28 through the rear portion 22. A shoulder 42 is defined at the junction of passages 38 and 40. As shown in FIGS. 4 and 5, a cylindrical tube or ferrule 44 preferably made of steel is positioned within the passage 40 and abuts against the shoulder 42. The ferrule includes a passage which is coaxial with and substantially the same in diameter as the passage 38 through the tubular body 34. The outside diameter of the ferrule is sufficiently large that it frictionally engages the walls defining the passage 40.

As the guidewire 14 exits dispenser tube 12, it passes through passage 28 and into the slot 32C. Upon exiting the rear portion 22, it passes externally through the opening 46 defined by the curved members 32. The guidewire 14 then enters the slot 32D from where it is directed into passage 38 by a generally conical portion 48. It finally passes into the steel ferrule 44. The guidewire is preferably, but not necessarily, substantially coplanar with the bowed members as well as coaxial with the lonqitudinal axis extending through the passages 28,38.

As the guidewire 14 is easily accessible from the sides via opening 46, it can easily be grasped between a thumb and finger of the user, thereby allowing the user to advance or retract the guidewire. The opening 46 may have a length of about an inch to an inch and a half and a maximum width between about one half and three quarters of an inch. The ability to easily engage guidewire 14 between two fingers allows the user to be able to finely manipulate the guidewire, including rotating it if desired.

Figure 10:
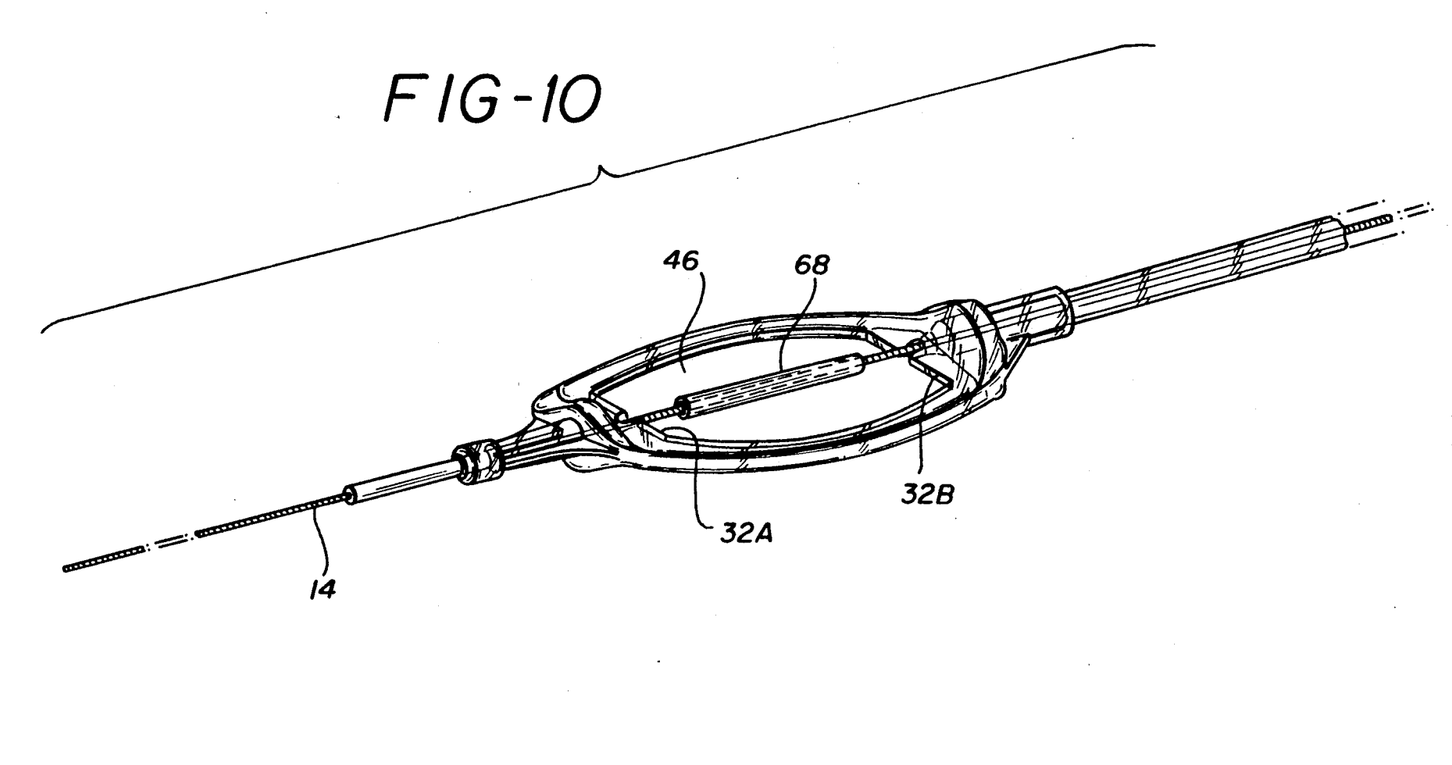
FIG. 10 is a top perspective view of an alternative embodiment of the present invention, including a slidable flexible sheath carried on the guidewire in the open portion.

Sheath 68 provides a grip with which to advance retract guidewire 14 to enable it to be more easily held. It also shields guidewire 16 so that the risk of its contamination will be reduced.

FIG. 8 depicts the insertion of the guidewire into a blood vessel 50. A cannula 54 of an introducer catheter 52 is first inserted into the blood vessel 50. The introducer catheter 52 includes an adapter 56 which remains external to the body. The end portion 18 of the guidewire 14 is first retracted into the ferrule 44 of the guidewire introducer 16, thereby straightening the end portion 18. The ferrule 44 and enlarged end portion 36 of the guidewire introducer 16 are then inserted into the adapter 56 The enlarged end portion 36 may maintain a friction fit with adapter 56, thereby providing for a stable connection during the insertion procedure. Once the enlarged end portion 36 is inserted into the adapter 56, the user grasps guidewire 14 between his thumb and finger. The guidewire 14 can then be advanced through thumb and finger pressure into the blood vessel 50. In addition, guidewire 14 can be finely manipulated and easily rotated if necessary. This motion may be repeated until the guidewire is in the desired position. The entire introducer assembly 10, including the dispenser tube 12, can be removed as a unit leaving the guidewire 14 in place. A catheter (not shown) is then introduced over the guidewire and into the blood vessel. Finally, the guidewire is removed.

Figure 9:
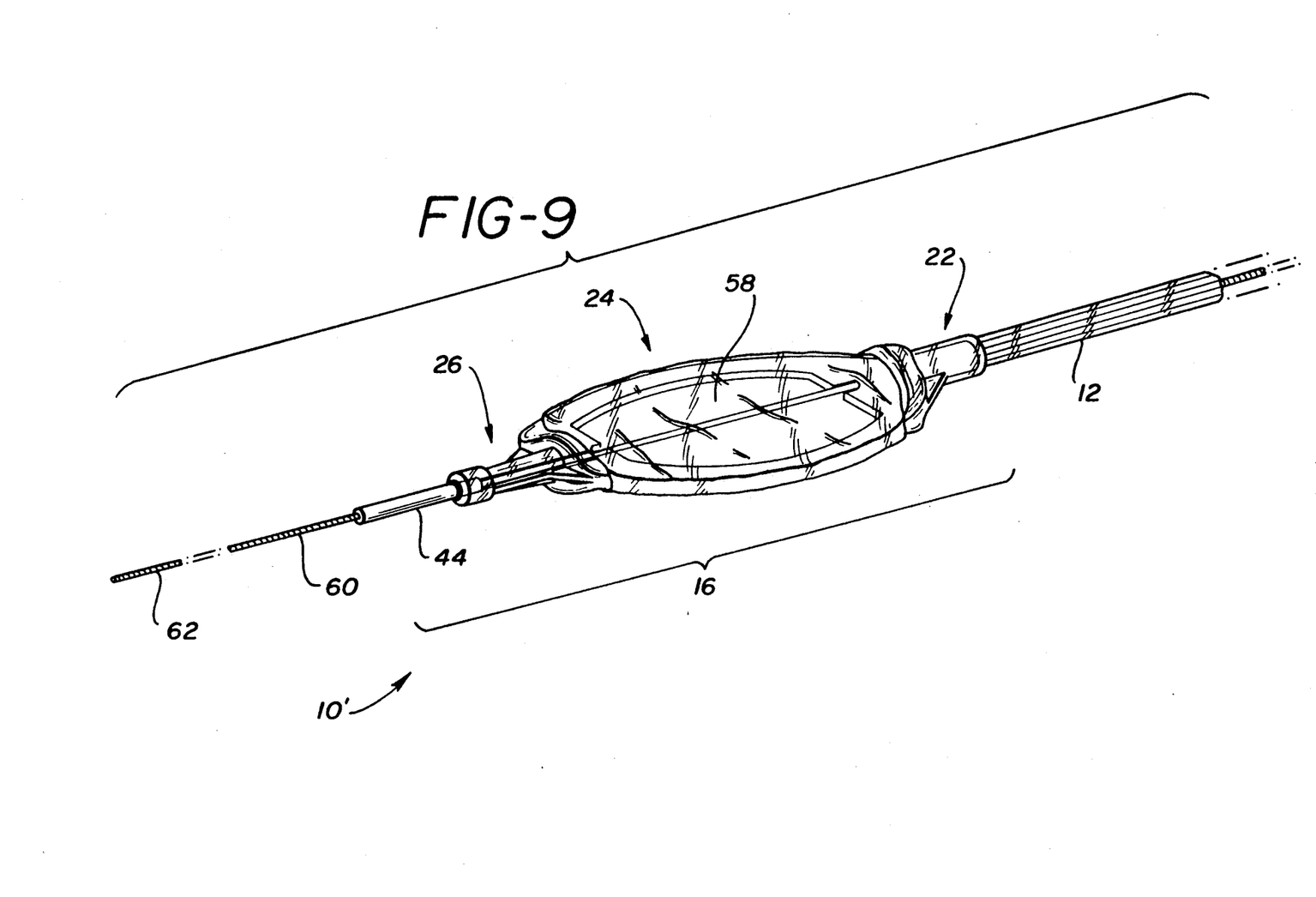
FIG. 9 is a top perspective view of an alternative embodiment of the present invention including a flexible enclosure for protecting the open portion of the guidewire introducer.

An alternative embodiment of the present invention is shown in FIG. 9. The same numerals are employed to designate the same elements previously described with respect to FIGS. 1-8. Illustrated therein is a guidewire introducer assembly 10' having a flexible covering 58 enclosing the guidewire introducer 16 to avoid touch contamination of the guidewire 14 during advancement. The covering is preferably made from a transparent film. An excess of film material is employed to facilitate advancing or retracting the guidewire.

In an alternative embodiment shown in FIG. 10, a sheath 68 may be placed in opening 46 so that guidewire 14 passes through sheath 68 Sheath 68 may be made of a soft, flexible substance such as silicone, polyurethane or PVC. The diameter of sheath 68 is such that sheath 68 can slide along guidewire 14, restrained in its scope of movement by webs 32A and 32B. The flexibility of sheath 68 enables it to be squeezed between the thumbs and forefinger so that the inner wall of sheath 68 grips guidewire 14 Guidewire 14 can be advanced by quipping sheath 68 and sliding guidewire 14 until sheath 68 strikes web 32A or 32B. When sheath 68 strikes webs 32A or 32B, it may be slid towards the web opposite to the web it struck and the guidewire 14 may be advanced or retracted by repeating the aforementioned steps.

While a guidewire having a J-tip end portion is employed in accordance with the preferred embodiment of the invention, the catheter introducer may also be employed in conjunction with a straight tipped guidewire 60, having a straight end portion 62.

Many other variations and modifications of the invention will be apparent to those skilled in the art without departing from the spirit and scope of the invention. The above described embodiment is, therefore, intended to be merely exemplary, and all such variations and modifications are intended to be included within the scope of the invention as defined in the appended claims.

What is claimed is:

1. A guidewire introducer assembly comprising:
   a guidewire; and
   a guidewire introducer including:
   a first end portion, and a second end portion, the guidewire extending between the first end portion and the second end portion;
   discrete first and second intermediate members connecting the first and second end portions, the first and second intermediate members lying substantially on opposite sides of the guidewire and spoiled apart from each other;
   a first passage extending through the first end portion and a second passage extending through the second end portion, the passages being aligned along an axis and adapted to permit the guidewire to pass axially therethrough and to rotate about the axis and beginning with a new line added--said assembly further comprising a cylindrical tube secured to and extending from the second end portion of said guidewire introducer, the cylindrical tube including a passage which is substantially coaxial with the second passage, the guidewire extending into the passage within the cylindrical tube.

2. The assembly of claim 1, wherein at least one of said intermediate members is bowed.

3. The assembly of claim 1, wherein at least one of said intermediate members has a wedge-shaped cross-sectional configuration to facilitate access to the guidewire.

4. The assembly of claim 1, further comprising a dispenser tube adapted to receive the guidewire, wherein the first end portion of said guidewire introducer is adapted to be interconnected with said dispenser tube.

5. The assembly of claim 4, wherein said guidewire introducer is rotatable with respect to said dispenser tube.

6. The assembly of claim 1 further comprising a cannula disposed in the second passage so that said guidewire can be fed through said guidewire introducer and said cannula.

7. The assembly of claim 1 wherein said second end portion comprises means for interconnecting said guidewire introducer to a luer connector.

8. The assembly of claim 1, further comprising a cover secured to said first and second intermediate members such that the cover permits the guidewire to be manipulated by exerting pressure upon the cover.

9. The assembly of claim 8, wherein said cover is flexible.

10. The assembly of claim 1, further comprising sheath means carried by said guidewire between the first and second intermediate members.

11. The assembly of claim 10 wherein said sheath means covers substantially half of said guidewire between the first and second intermediate members.

12. The assembly of claim 10 wherein said sheath means permits said guidewire to be grasped by grasping said sheath means.

13. The assembly of claim 10 wherein said sheath means is slidable on said guidewire.

14. The assembly of claim 1 wherein the first and second intermediate members are spaced apart such that the guidewire can be held between a thumb and forefinger of a user.

* * * * *